(12) United States Patent
Hashi

(10) Patent No.: US 12,133,628 B2
(45) Date of Patent: Nov. 5, 2024

(54) MEDICAL DEVICE

(71) Applicant: OLYMPUS CORPORATION, Tokyo (JP)

(72) Inventor: Hiroshi Hashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 908 days.

(21) Appl. No.: 17/156,755

(22) Filed: Jan. 25, 2021

(65) Prior Publication Data
US 2021/0145256 A1  May 20, 2021

Related U.S. Application Data (63) Continuation of application No. PCT/JP2018/028214, filed on Jul. 27, 2018.

(51) Int. Cl.
*A61B 1/00* (2006.01)
*A61B 1/015* (2006.01)

(52) U.S. Cl.
CPC ...... *A61B 1/00082* (2013.01); *A61B 1/00112* (2013.01); *A61B 1/00135* (2013.01); *A61B 1/015* (2013.01)

(58) Field of Classification Search
CPC ............ A61B 1/00082; A61B 1/00154; A61B 1/00156; A61B 1/00135; A61B 1/00112; A61B 1/015; A61M 2025/1072
See application file for complete search history.

(56) References Cited

U.S. PATENT DOCUMENTS

| | | | | |
|---|---|---|---|---|
| 5,364,353 | A | * | 11/1994 | Corfitsen ................ F16L 55/26 600/116 |
| 2008/0033246 | A1 | * | 2/2008 | Matsui ............... A61B 1/00082 600/115 |
| 2010/0240955 | A1 | | 9/2010 | Sinai et al. |

(Continued)

FOREIGN PATENT DOCUMENTS

| | | |
|---|---|---|
| EP | 2959934 A1 | 12/2015 |
| JP | H05-063550 U | 8/1993 |

(Continued)

OTHER PUBLICATIONS

International Search Report dated Oct. 30, 2018 issued in PCT/JP2018/028214.

*Primary Examiner* — Timothy J Neal
(74) *Attorney, Agent, or Firm* — Scully, Scott, Murphy & Presser, P.C.

(57) ABSTRACT

The present invention provides a medical device including: an insertion part having a longitudinal axis; a first balloon and a second balloon attached to the insertion part; and a fluid supply path through which a fluid is supplied to the first balloon and the second balloon. The first balloon can be expanded and contracted and is movable in the longitudinal-axis direction. The second balloon can be expanded and contracted and is disposed closer to a distal end side than the first balloon is. One end of the second balloon is fixed to the distal end of the insertion part, and the other end of the second balloon is fixed to the first balloon. The fluid supply path has a connecting flow path communicating between the first balloon and an inner space of the second balloon. The second balloon is expanded after the first balloon is expanded, by supplying the fluid.

20 Claims, 8 Drawing Sheets

(56) References Cited

U.S. PATENT DOCUMENTS

| | | |
|---|---|---|
| 2010/0249505 A1* | 9/2010 | Shoham ............ A61M 25/0116 600/115 |
| 2011/0245858 A1 | 10/2011 | Milsom et al. |
| 2013/0338440 A1 | 12/2013 | Sinai et al. |
| 2015/0133774 A1 | 5/2015 | Milsom et al. |
| 2015/0150436 A1 | 6/2015 | Cornhill et al. |
| 2015/0351618 A1 | 12/2015 | Tanikawa et al. |
| 2016/0278626 A1 | 9/2016 | Cornhill et al. |
| 2018/0035872 A1 | 2/2018 | Cruz et al. |
| 2019/0069761 A1 | 3/2019 | Milsom et al. |
| 2019/0133420 A1 | 5/2019 | Cornhill et al. |
| 2019/0335982 A1 | 11/2019 | Johann et al. |
| 2019/0343372 A1 | 11/2019 | Cornhill et al. |
| 2020/0022562 A1 | 1/2020 | Milsom et al. |
| 2020/0121168 A1 | 4/2020 | Milsom et al. |
| 2020/0146530 A1 | 5/2020 | Cruz et al. |
| 2020/0245848 A1 | 8/2020 | Johann et al. |

FOREIGN PATENT DOCUMENTS

| | | |
|---|---|---|
| JP | H07-265412 A | 10/1995 |
| JP | 2006-223895 A | 8/2006 |
| JP | 2011-501682 A | 1/2011 |
| JP | 2011-234746 A | 11/2011 |
| JP | 2012-075595 A | 4/2012 |
| JP | 2014-161385 A | 9/2014 |
| WO | WO 2009/050668 A2 | 4/2009 |
| WO | WO 2011/084490 A1 | 7/2011 |
| WO | WO 2015/123313 A1 | 8/2015 |
| WO | WO 2016/193820 A1 | 8/2016 |
| WO | WO 2018/064343 A1 | 4/2018 |
| WO | WO 2018/132836 A1 | 7/2018 |
| WO | WO 2018/156768 A1 | 8/2018 |
| WO | WO 2020/018566 A1 | 1/2020 |
| WO | WO 2020/132680 A1 | 6/2020 |

* cited by examiner

MEDICAL DEVICE

CROSS-REFERENCE TO RELATED APPLICATIONS

This is a continuation of International Application PCT/JP2018/028214, with an international filing date of Jul. 27, 2018, which is hereby incorporated by reference herein in its entirety.

TECHNICAL FIELD

The present invention relates to a medical device.

BACKGROUND ART

A known device prevents the inconvenience that, when a medical device, such as an endoscope or an overtube, is inserted into the large intestine, the intestinal tract moves with the medical device due to friction or the like with the inner wall of the large intestine, and thus, the medical device cannot be advanced relative to the intestinal tract (for example, see Japanese Unexamined Patent Application, Publication No. 2012-75595).

This device includes two first balloons that are disposed at a distance from each other in the longitudinal-axis direction of the medical device and are each capable of expanding and contracting in the radial direction, and a second balloon that is disposed between the two first balloons and is capable of expanding and contracting in the longitudinal-axis direction.

When the medical device is to be advanced inside the intestinal tract by using this device, first, the first balloon attached on the distal end side of the medical device is expanded, the first balloon on the base-end side is contracted, and the second balloon is contracted. This allows the base-end-side first balloon to advance toward the distal-end-side first balloon by using the distal-end-side first balloon as a reference.

Next, in a state in which the base-end-side first balloon is expanded and the distal-end-side first balloon is contracted, the second balloon is expanded. This allows the distal-end-side first balloon to be pushed forward by using the base-end-side first balloon as a reference and thus allows the distal end of the medical device, to which the first balloon is fixed, to advance relative to the intestinal tract.

SUMMARY OF INVENTION

An aspect of the present invention is a medical device including: an insertion part to be inserted into a body cavity, the insertion part having a longitudinal axis; a first balloon and a second balloon attached to the insertion part; and a fluid supply path through which a fluid is supplied to or discharged from the first balloon and the second balloon. The first balloon can be expanded and contracted by the fluid in a direction intersecting the longitudinal axis and is supported so as to be movable in a longitudinal-axis direction relative to the insertion part. The second balloon can be expanded and contracted by the fluid in the longitudinal-axis direction and is disposed closer to a distal end side than the first balloon is in the longitudinal-axis direction. One end of the second balloon is fixed to the distal end of the insertion part, and the other end of the second balloon is fixed to the first balloon. The fluid supply path has a connecting flow path communicating between an inner space of the first balloon and an inner space of the second balloon. The second balloon is expanded after the first balloon is expanded, by supplying the fluid through the fluid supply path.

DESCRIPTION OF EMBODIMENTS

A medical device 1 according to an embodiment of the present invention will be described below with reference to the drawings.

Figure 1:
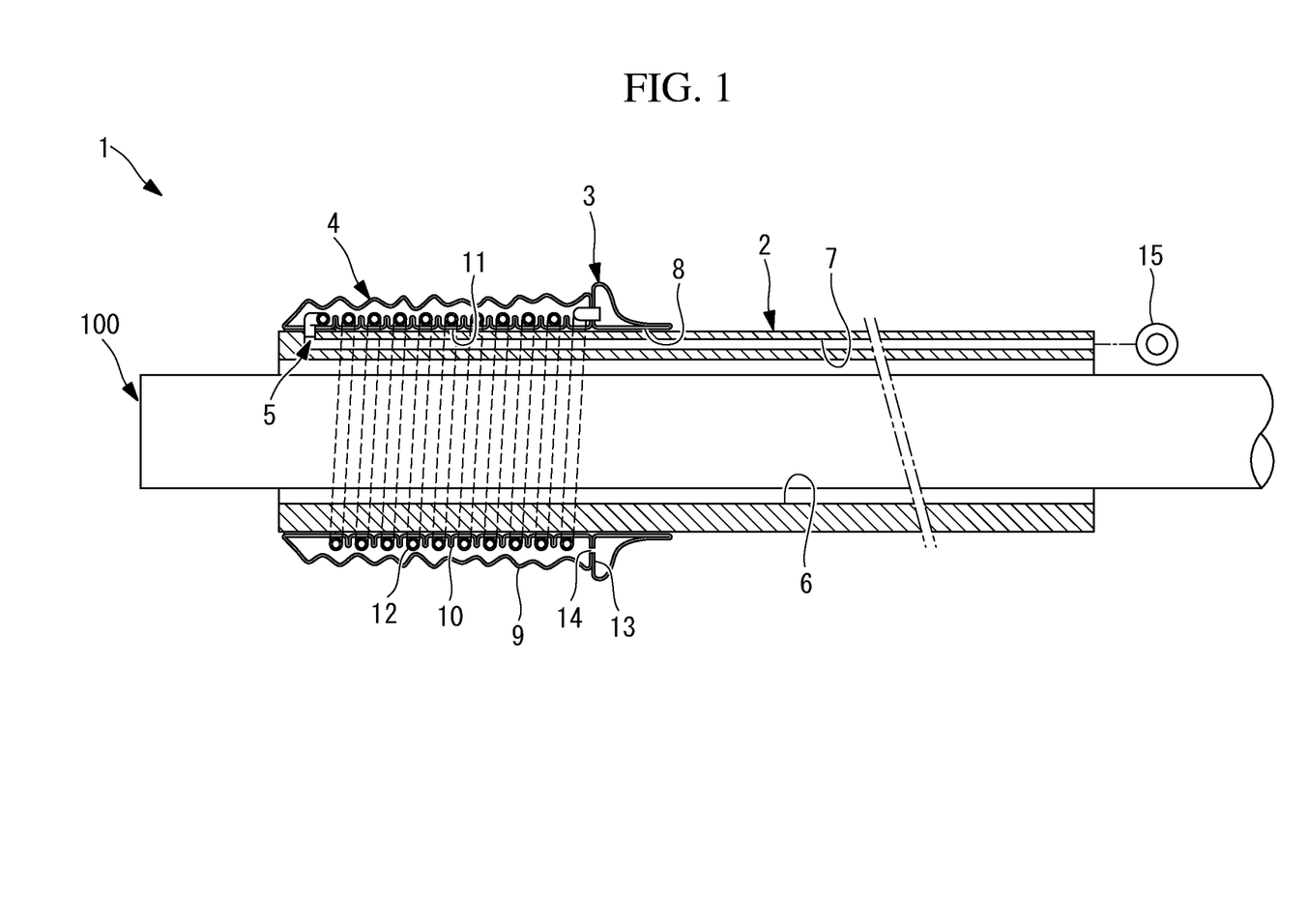
FIG. 1 is a vertical cross section showing a state in which balloons of a medical device according to an embodiment of the present invention are contracted.

As shown in FIG. 1, the medical device 1 according to this embodiment is an overtube and includes a flexible insertion part 2 having a longitudinal axis, a first balloon 3 and a second balloon 4 attached to the insertion part 2, and a single fluid supply path 5 through which a fluid, such as pressurized air, is supplied to or discharged from the first balloon 3 and the second balloon 4.

The insertion part 2 has a through-hole 6 penetrating in the longitudinal-axis direction along the central axis, through which the endoscope 100 can be inserted, and a supply hole 7 (described below).

The first balloon 3 is formed in a ring shape and has a center hole 8 having a greater inside diameter than the outside diameter of the insertion part 2. The first balloon 3 is expanded radially outward over the entire circumference when the fluid is supplied thereto.

The second balloon 4 is formed in a cylindrical shape in which an outer tube (tubular part) 9 and an inner tube (tubular part) 10 having different outside diameters are concentrically disposed and in which both ends in the axial direction are closed. The inner tube 10 has a center hole 11 having an inside diameter that is greater than the outside diameter of the insertion part 2. The inner tube 10 and the outer tube 9 contract in the axial direction when corrugated and expand in the axial direction when smoothed out. With this structure, the second balloon 4 expands mainly in the axial direction when the fluid is supplied to the space between the inner tube 10 and the outer tube 9.

In a state in which the insertion part 2 passes through the center hole 11, the inner surface of the inner tube 10 of the second balloon 4 at one end is fixed to the outer surface of the vicinity of the distal end of the insertion part 2, and the other end is disposed so as to be movable in the longitudinal-axis direction relative to the insertion part 2.

The first balloon 3 is fixed to the other end of the second balloon 4, which is movable in the longitudinal-axis direction relative to the insertion part 2. The outside diameter of the first balloon 3 when expanded is set to be greater than the outside diameter of the second balloon when expanded.

The fluid supply path 5 includes the supply hole 7 provided in the insertion part 2, a tube 12 that is connected to the supply hole 7 at a position where the second balloon 4 is fixed to the insertion part 2 and that is disposed inside the second balloon 4, and a connecting flow path 14 penetrating through a partition wall 13 between the first balloon 3 and the second balloon 4 to communicate between the inner spaces of the balloons 3 and 4.

The supply hole 7 extends in the longitudinal-axis direction from the base end to the proximity of the distal end of the insertion part 2, extends in the radial direction at the position where the second balloon 4 is fixed, and is open in the outer circumferential surface of the insertion part 2 to form a port.

The tube 12 is formed in a spiral shape disposed at a position surrounding the outer circumference of the inner tube 10 of the second balloon 4. One end of the tube 12 is connected to the port of the supply hole 7, and the other end of the tube 12 is connected to the first balloon 3 through the partition wall 13 between the first balloon 3 and the second balloon 4.

Figure 2:
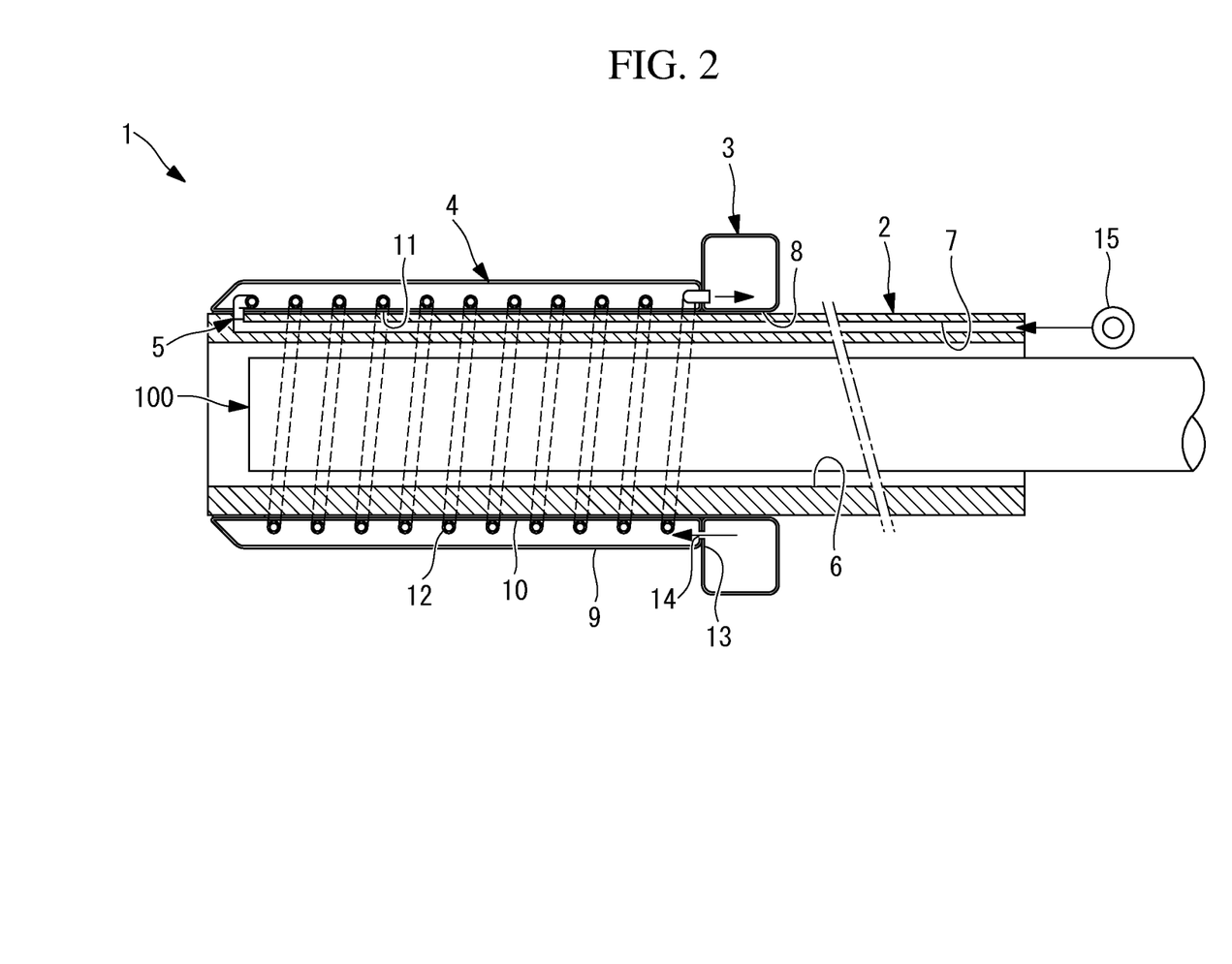
FIG. 2 is a vertical cross section showing a state in which the balloons of the medical device in FIG. 1 are expanded.

As shown in FIG. 2, in a state in which the second balloon 4 is expanded, the tube 12 is fixed to the outer circumferential surface of the smoothed inner tube 10. Hence, as shown in FIG. 1, in a state in which the second balloon 4 is contracted, the tube 12 is disposed between the pleats formed by contracting and corrugating the inner tube 10 in the axial direction.

In this embodiment, the aperture of the connecting flow path 14 communicating between the inner space of the first balloon 3 and the inner space of the second balloon 4 is configured to be sufficiently small. With this structure, the flow resistance of the fluid in the supply hole 7 and the tube 12 is set to be smaller than the flow resistance of the fluid in the connecting flow path 14.

The effects of the thus-configured medical device 1 according to this embodiment will be described below.

Figure 3:
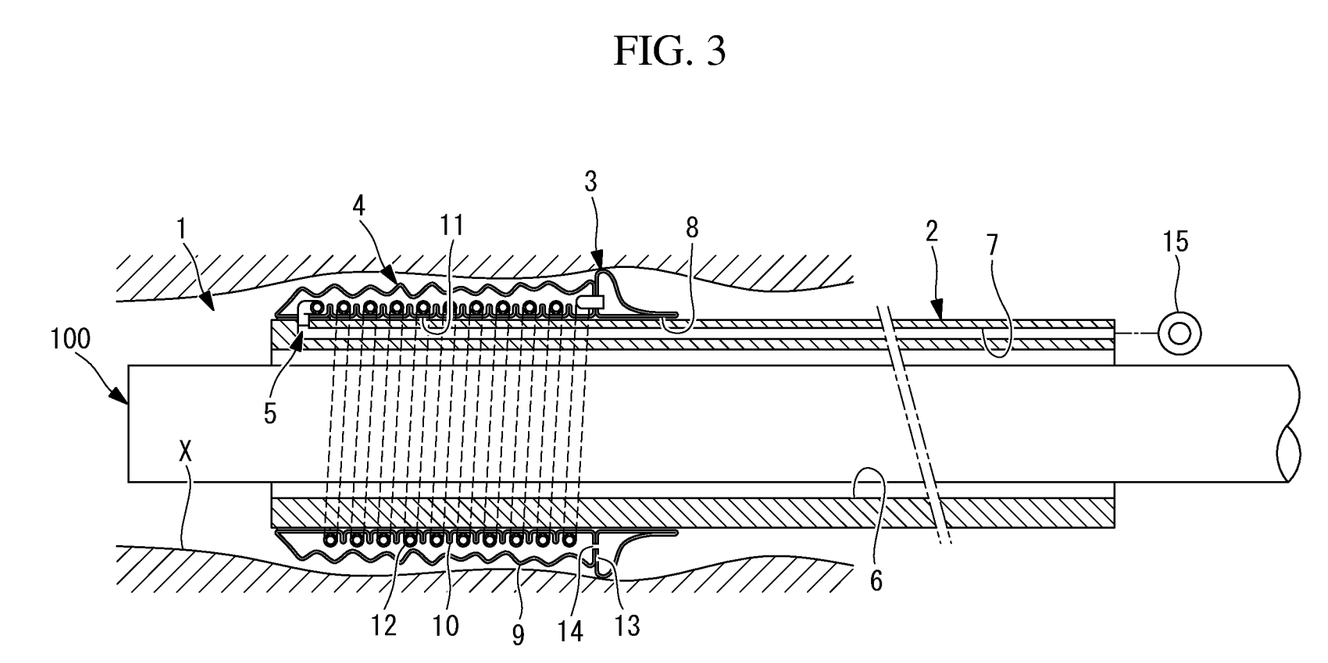
FIG. 3 is a vertical cross section showing a state in which the medical device in FIG. 1 is inserted into the large intestine.

When the overtube, which is the medical device 1 according to this embodiment, is inserted into the large intestine X, as shown in FIG. 1, in a state in which the endoscope 100 is inserted through the through-hole 6 in the insertion part 2, the endoscope 100 projecting from the distal end of the overtube 1 is inserted into the large intestine (body cavity) X, and then, as shown in FIG. 3, the overtube 1 is inserted into the large intestine X by using the endoscope 100 as a guide.

In advancing the overtube 1 through the large intestine X, when it becomes difficult to move the overtube 1 relative to the large intestine X due to the friction between the large intestine X and the overtube 1, a fluid is supplied to the inside of the first balloon 3, through the fluid supply path 5, from a fluid supply source 15 connected to the base end of the supply hole 7 provided at the base end of the insertion part 2.

Specifically, when the fluid is supplied from the base end of the supply hole 7, the fluid is supplied to the distal end of the insertion part 2 through the supply hole 7 in the insertion part 2, flows into the tube 12 connected to the port provided at the distal end of the supply hole 7, and flows into the first balloon 3 through the tube 12.

Figure 4:
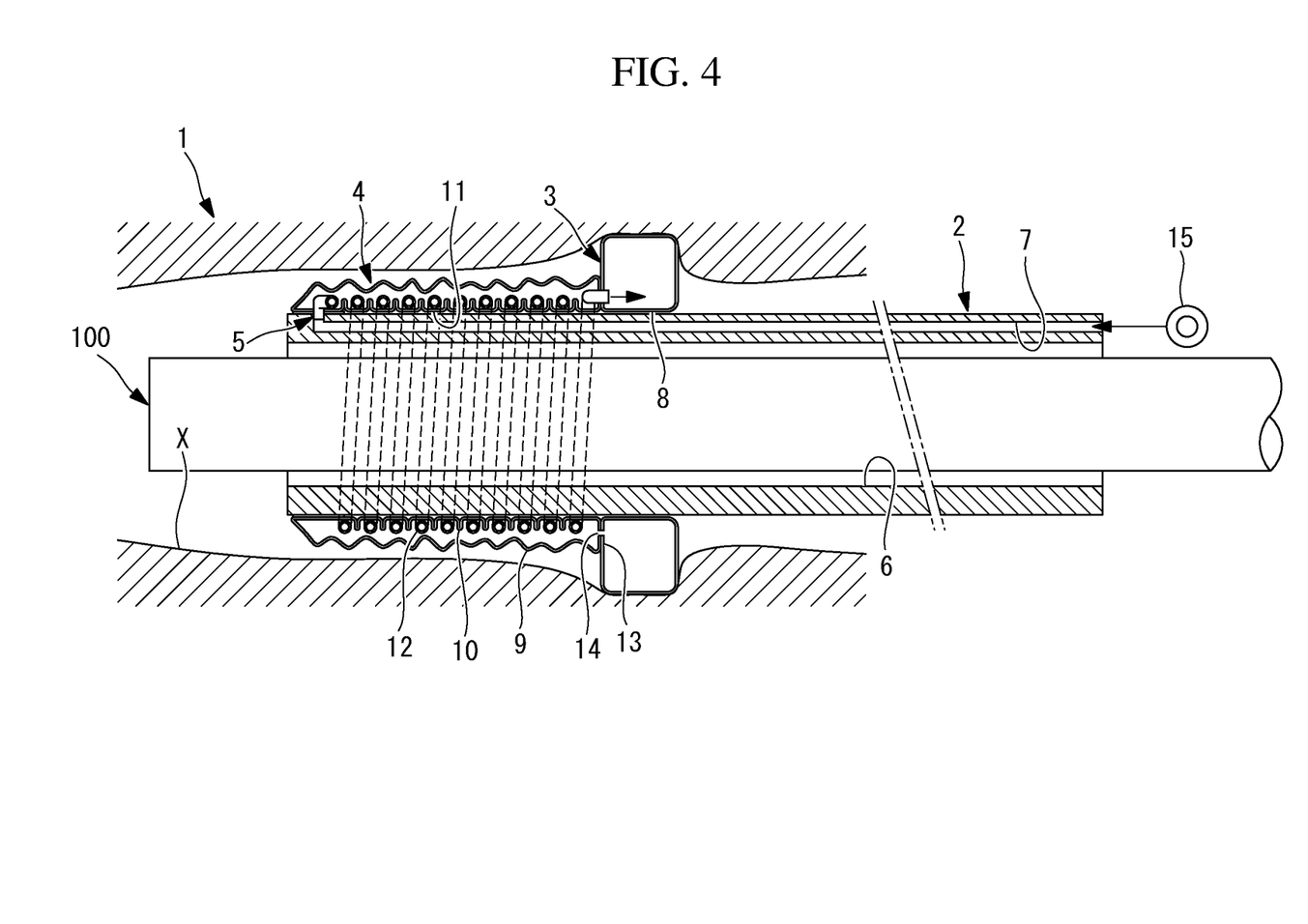
FIG. 4 is a vertical cross section showing a state in which a fluid is supplied to the medical device in FIG. 3 to expand the first balloon.

Because the flow resistance in the supply hole 7 and the tube 12 is set to be smaller than the flow resistance in the connecting flow path 14, the flow rate of the fluid flowing into the first balloon 3 is greater than the flow rate of the fluid flowing out to the second balloon 4 through the connecting flow path 14. Hence, as shown in FIG. 4, the first balloon 3 is expanded first.

The first balloon 3 is expanded radially outward when the fluid is supplied thereto. As a result, the outer circumferential surface of the first balloon 3 pushes the inner surface of the intestinal wall of the large intestine X outward, and thus, the first balloon 3 is fixed to the large intestine X due to the increased friction with the large intestine X.

Figure 5:
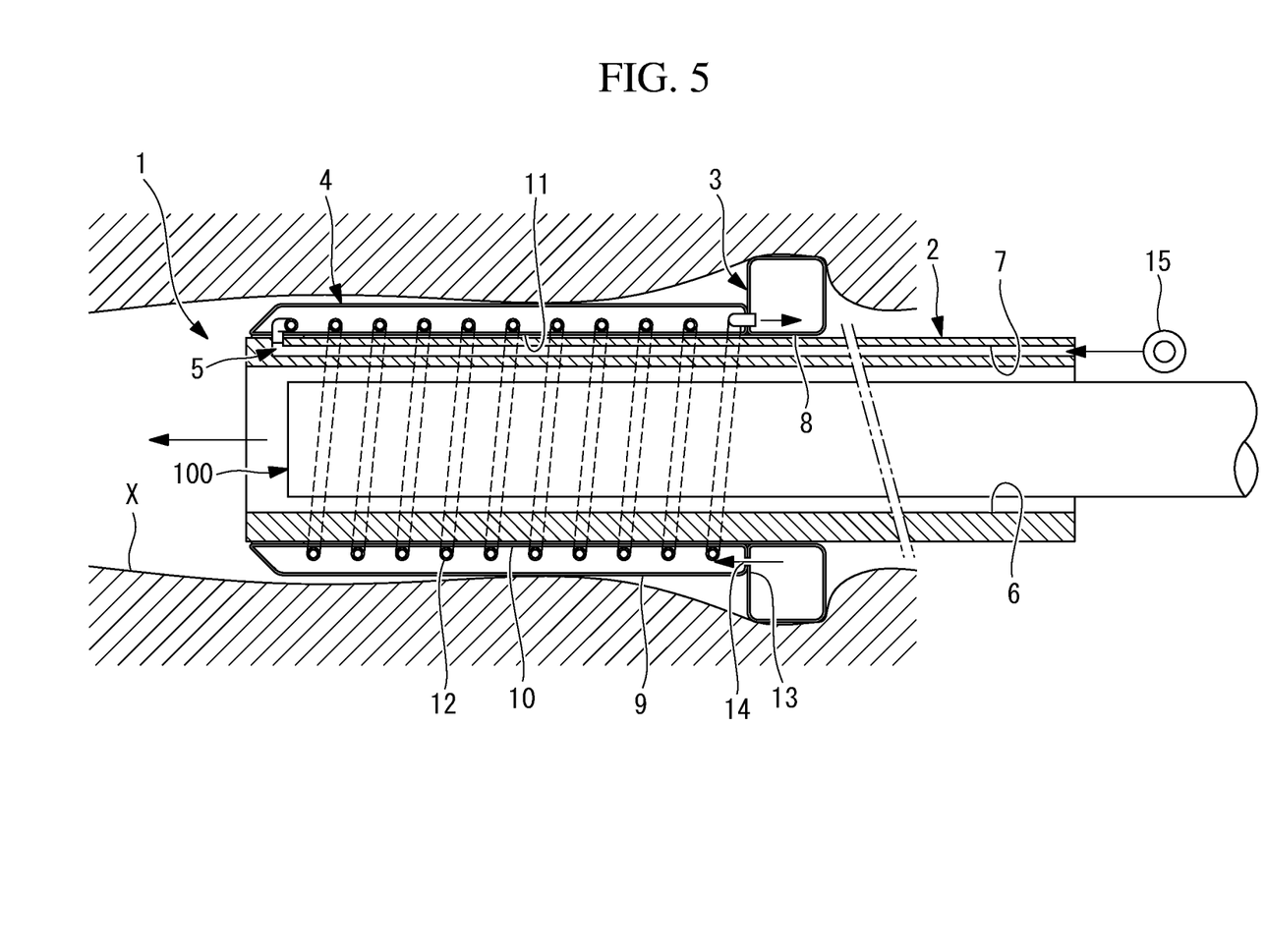
FIG. 5 is a vertical cross section showing a state in which more fluid is supplied to the medical device in FIG. 4 to expand the second balloon, and an overtube is advanced inside the large intestine.

When the fluid continues to be further supplied from the fluid supply source 15, the fluid, after expanding the first balloon 3, flows into the second balloon 4 through the connecting flow path 14, expanding the second balloon 4, as shown in FIG. 5. The second balloon 4 is expanded in the axial direction by the fluid supplied thereto. Hence, as the second balloon 4 fixed between the first balloon 3 and the distal end of the insertion part 2 expands, the distance between the first balloon 3 and the distal end of the insertion part 2 increases.

Specifically, because the first balloon 3 is fixed to the large intestine X, the distal end of the insertion part 2 is advanced in the direction away from the first balloon 3 as the second balloon 4 expands. As a result, it is possible to effectively advance the insertion part 2, that is, the overtube 1, relative to the large intestine X.

When the insertion part 2 is not sufficiently advanced relative to the large intestine X, the supply of the fluid from the fluid supply source 15 to the supply hole 7 is stopped, and the fluid is discharged through the supply hole 7. As a result, the fluid in the balloons 3 and 4 is discharged to the base-end side of the insertion part 2 through the tube 12 and the supply hole 7. Also in this case, because the flow resistance in the supply hole 7 and the tube 12 is set to be smaller than the flow resistance in the connecting flow path 14, the fluid in the first balloon 3 is discharged first, contracting the first balloon 3, and then the fluid in the second balloon 4 is discharged, contracting the second balloon 4.

Specifically, because the second balloon 4 contracts in the axial direction after the first balloon 3 contracts in the radial direction, and thus the outer circumferential surface of the first balloon 3 is separated from the inner surface of the intestinal wall of the large intestine X, that is, the fixed state therebetween is released, the first balloon 3 is pulled toward the distal end of the insertion part 2. As a result, the first balloon 3 can be moved further toward the deeper part.

In this case, with the medical device 1 according to this embodiment, because the fluid supply path 5 leading to the first balloon 3 and the second balloon 4 is a single flow path having the supply hole 7, the tube 12, and the connecting flow path 14, the structure is simple and the configuration is easy, compared with a case where separate flow paths are provided. There is an advantage in that it is possible to gradually move the overtube 1 to the deeper part relative to the large intestine X, simply by repeatedly switching between supply and discharge of the fluid through this single fluid supply path 5.

Because the supply hole 7 is provided inside the tube wall of the insertion part 2, and the tube 12 is provided inside the second balloon 4, a pipe for supplying fluid does not need to be exposed outside. Hence, it is possible to prevent the inconvenience that the pipe is caught by the intestinal wall.

Because the tube 12 is disposed in a spiral shape, there is an advantage in that it is possible to smoothly respond to dimensional changes in the axial direction caused by expanding and contracting of the second balloon 4 and, thus, to smoothly supply and discharge the fluid to and from the first balloon 3.

It is also possible to push the inner wall of the body cavity with the first balloon 3 to move the inner wall of the body cavity. By doing so, by fixing the first balloon 3 to the body wall of an organ having creases in the body wall and expanding the second balloon 4, it is possible to move the body wall to smooth out the creases, thus achieving a state in which observation and treatment of the body wall are easy. Because the body wall alone can be moved without changing the position of the insertion part 2, it is possible to bring the body wall located at a far position to a near position.

Although the flow resistance is adjusted by reducing the size of the aperture of the connecting flow path 14 in this embodiment, instead, the flow resistance may be adjusted by providing, in the connecting flow path 14, a valve that is opened when the pressure in the first balloon 3 exceeds a predetermined pressure.

Figure 6:
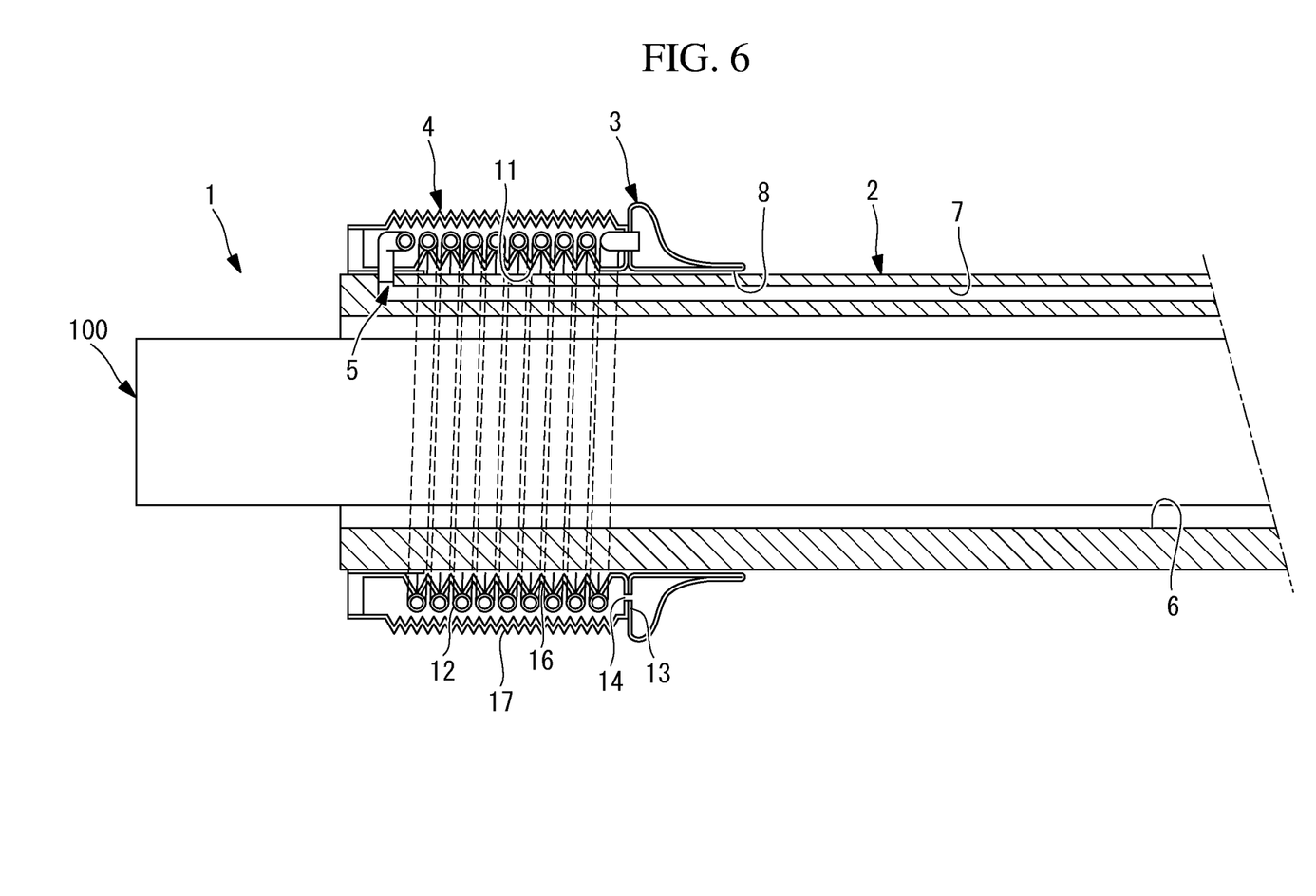
FIG. 6 is a vertical cross section showing a first modification of the medical device in FIG. 1.

Although an example case in which the second balloon 4 has the inner tube 10 and the outer tube 9 that are corrugated when the second balloon 4 is contracted has been described, instead, as shown in FIG. 6, a structure may be employed in which the second balloon 4 has two coaxially disposed bellows 16 and 17 that have different outside diameters and can expand and contract in the axial direction. In that case, by fixing the tube 12 on the maximum-diameter portions of the inner bellows 16, the tube 12 can be prevented from being nipped by the inner bellows 16 when the inner bellows 16 are expanded and contracted. The inner bellows 16 having a spiral shape are more desirable.

Figure 7:
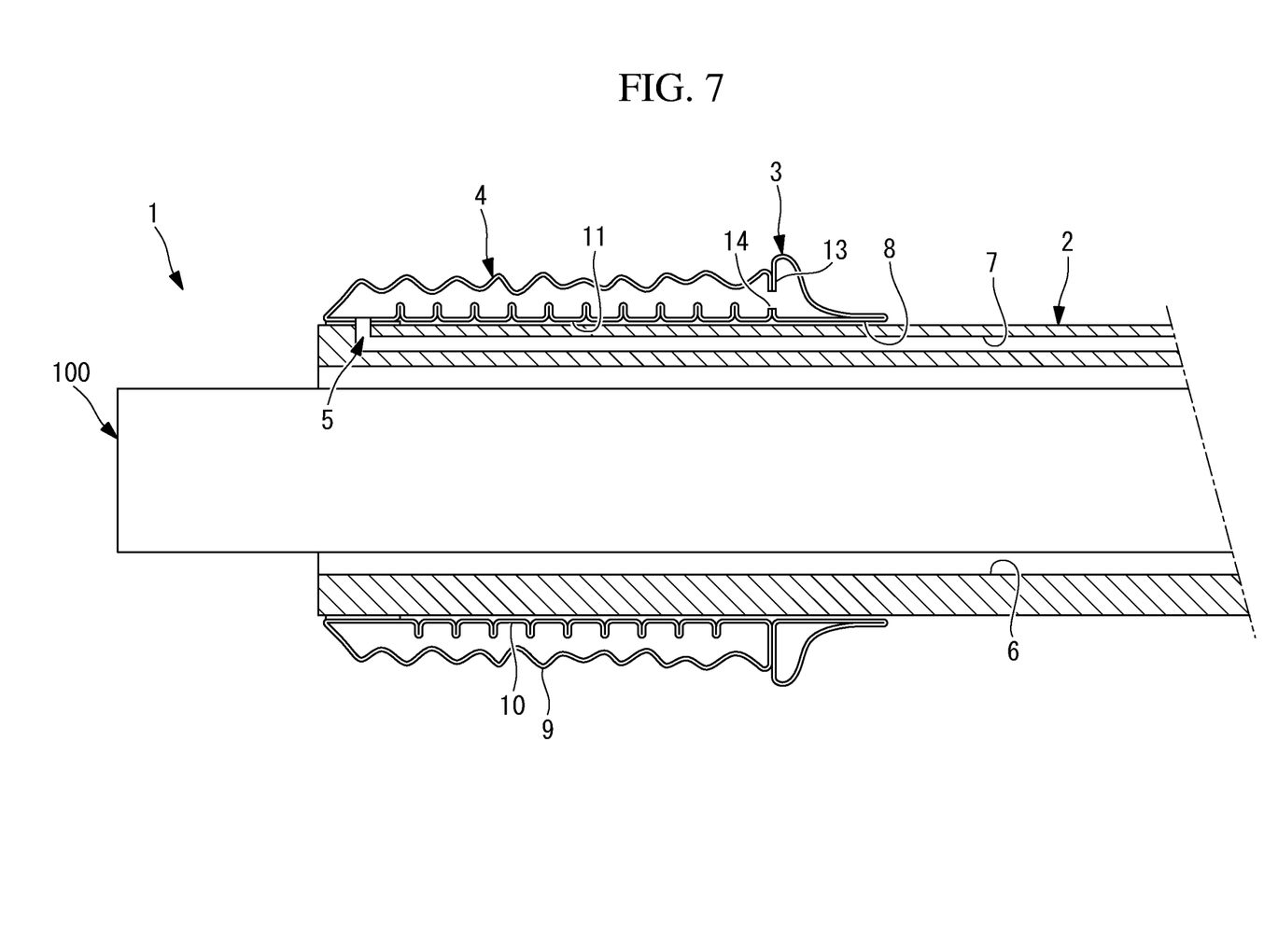
FIG. 7 is a vertical cross section showing a second modification of the medical device in FIG. 1.

Although an example case in which the fluid supply path 5 has the tube 12 connecting the port and the first balloon 3 has been described in this embodiment, the structure is not limited thereto, and, as shown in FIG. 7, the tube 12 may be omitted. In that case, the second balloon 4 is made of a material having a higher modulus of elasticity than the first balloon 3, and the connecting flow path 14 is formed in a relatively large size.

Specifically, with this structure, when the fluid is supplied from the port to the inside of the second balloon 4, the supplied fluid also enters the first balloon 3 through the connecting flow path 14. Hence, the pressures inside the first balloon 3 and the second balloon 4 become equal. By making the second balloon 4 of a material having a higher modulus of elasticity than the first balloon 3, the first balloon 3 is more easily expanded than the second balloon 4 is with the same pressure. Thus, it is possible to expand the first balloon 3 first and then the second balloon 4.

Figure 8:
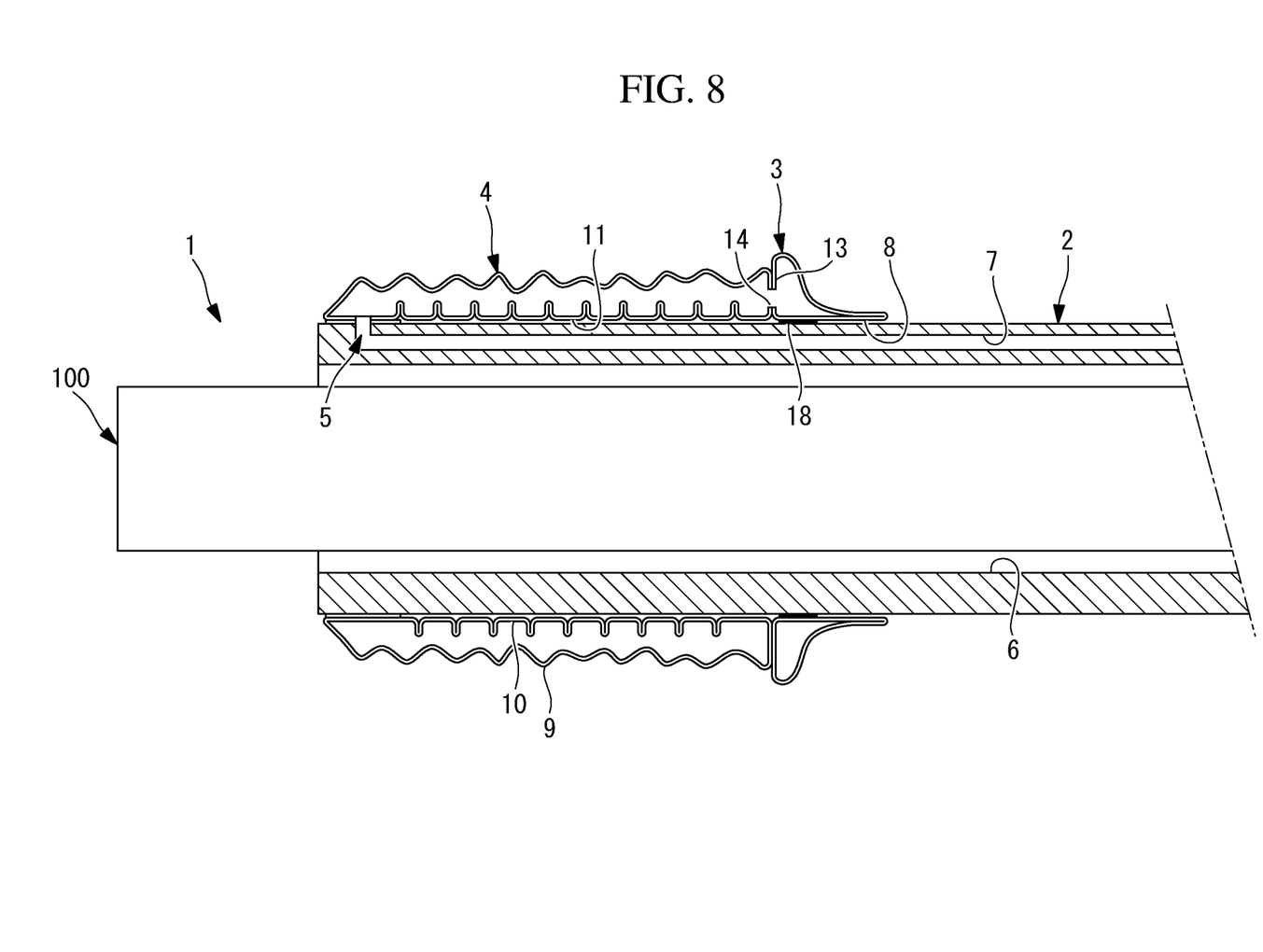
FIG. 8 is a vertical cross section showing a third modification of the medical device in FIG. 1.

It is also possible that the tube 12 is omitted, the connecting flow path 14 is formed in a relatively large size, the first balloon 3 and the second balloon 4 are formed of the same material, and, as shown in FIG. 8, the inner surface of the first balloon 3 is temporarily fixed to the outer surface of the insertion part 2 with an arbitrary temporary fixing part 18, which employs bonding, engaging, or the like. In that case, fixing between the inner surface of the first balloon 3 and the outer surface of the insertion part 2, temporarily fixed by the temporary fixing part 18, is released at the point when the first balloon 3 and the second balloon 4 expand, and the propulsive force produced by the expansion of the second balloon 4 exceeds a predetermined threshold. Also with this structure, it is possible to expand the first balloon 3 first and then the second balloon 4.

Although the overtube 1 has been described as an example of the medical device in this embodiment, instead, the present invention may be applied to an endoscope 100.

Although the large intestine X has been described as an example body cavity into which the medical device 1 is inserted, the present invention may be applied to a medical device 1 to be inserted into another arbitrary body cavity.

As a result, the following aspect is read from the above described embodiment of the present invention.

An aspect of the present invention is a medical device including: an insertion part to be inserted into a body cavity, the insertion part having a longitudinal axis; a first balloon and a second balloon attached to the insertion part; and a fluid supply path through which a fluid is supplied to or discharged from the first balloon and the second balloon. The first balloon can be expanded and contracted by the fluid in a direction intersecting the longitudinal axis and is supported so as to be movable in the longitudinal-axis direction relative to the insertion part. The second balloon can be expanded and contracted by the fluid in the longitudinal-axis direction and is disposed closer to a distal end side than the first balloon is in the longitudinal-axis direction. One end of the second balloon is fixed to the distal end of the insertion part, and the other end of the second balloon is fixed to the first balloon. The fluid supply path has a connecting flow path communicating between an inner space of the first balloon and an inner space of the second balloon. The second balloon is expanded after the first balloon is expanded, by supplying the fluid through the fluid supply path.

According to this aspect, when the insertion part is inserted into the body cavity from the distal end side, the insertion part cannot be effectively inserted into the body cavity due to the friction with the inner wall of the body cavity. In this case, by supplying the fluid to the first balloon and the second balloon through the fluid supply path, the first balloon on the base-end-side expands first and is fixed to the inner wall of the body cavity due to the increased friction with the inner wall of the body cavity.

Subsequently, as a result of the second balloon expanding in the longitudinal-axis direction of the insertion part, the insertion part, to which one end of the second balloon is fixed, is pushed out forward in the longitudinal-axis direction relative to the first balloon, to which the other end of the second balloon is fixed. As a result, the distal end of the insertion part is advanced in a state in which the inner wall of the body cavity is held by the first balloon, and thus, the insertion part can be effectively inserted into the body cavity.

According to this aspect, it is also possible to push the inner wall of the body cavity with the first balloon to move the inner wall of the body cavity. Hence, for example, by fixing the first balloon to the body wall of an organ having creases in the body wall and by expanding the second balloon, it is possible to move the body wall to smooth out the creases and thus to realize a state in which observation and treatment of the body wall are easy. Because the body wall alone can be moved without changing the position of the insertion part, it is possible to bring the body wall located at a far position to a near position.

In that case, because the fluid is supplied to or discharged from the first balloon and the second balloon through the common fluid supply path, it is possible to advance the insertion part in the body cavity more reliably and with a simpler structure, compared with a case in which separate supply paths are provided for the balloons.

In the above-described aspect, the outside diameter of the first balloon when expanded may be greater than the outside diameter of the second balloon when expanded.

With this structure, in a state in which the first balloon is expanded, while the outer circumferential surface of the first balloon is pressed against the inner wall of the body cavity, the outer circumferential surface of the second balloon is located away from the inner wall of the body cavity in the radial direction. This prevents the friction between the second balloon and the inner wall of the body cavity when the insertion part is moved, allowing the insertion part to be more smoothly advanced.

In the above-described aspect, the first balloon may be formed in a ring shape having a center hole, and the insertion part may be inserted through the center hole so as to be movable relative thereto in the longitudinal-axis direction.

With this structure, the first balloon is brought into tight contact with the inner wall of the body cavity over the entire circumference. As a result, the first balloon is kept more reliably fixed to the inner wall of the body cavity.

In the above-described aspect, the fluid supply path may have a tube through which the fluid is supplied to or discharged from the first balloon, and the flow resistance of the fluid having passed through the tube may be smaller than the flow resistance of the fluid having passed through the connecting flow path.

With this structure, the fluid to be supplied is supplied first to the first balloon through the tube and is then supplied from the inside of the first balloon to the inside of the second balloon through the connecting flow path. In that case, due to the difference in flow resistance, the supply of the fluid to the first balloon through the tube is likely to progress, and the supply of the fluid from the first balloon to the second balloon through the connecting flow path is delayed. As a result, it is possible to expand the first balloon first and then the second balloon with a simple structure.

In the above-described aspect, the tube may enter the inner space of the second balloon from the inside of the insertion part via a fixing position at which the second balloon is fixed to the insertion part and may be connected to the first balloon via the inner space of the second balloon.

With this structure, the tube can be arranged without being exposed to the outside of the insertion part, first balloon, and second balloon.

In the above-described aspect, the tube may have a spiral shape around the longitudinal axis.

With this structure, even when the second balloon expands in the longitudinal-axis direction, the tube connected to the first balloon through the second balloon is elastically deformed and extends in accordance with the expansion of the second balloon. Hence, it is possible to smoothly keep supplying the fluid to the first balloon.

In the above-described aspect, a valve that is opened when the pressure in the first balloon exceeds a predetermined pressure may be provided in the connecting flow path.

With this structure, the valve is kept closed when the pressure in the first balloon is less than or equal to the predetermined pressure. Hence, it is possible to more clearly realize the order of expansion of the first balloon and the second balloon.

In the above-described aspect, the inner space of the second balloon may be formed in a tubular shape by concentrically disposing two tubular parts having different outside diameters, and the tube may be attached to the radially outer surface of the tubular part located on the radially inner side.

With this structure, the tube can be disposed at a position where it does not inhibit the expansion and contraction of the second balloon.

In the above-described aspect, the fluid may be supplied to or discharged from either the first balloon or the second balloon through the fluid supply path, and the second balloon may be formed of a material having a higher modulus of elasticity than the first balloon.

With this structure, the fluid to be supplied is supplied to either one of the first balloon and the second balloon and is supplied to the other through the connecting flow path. In that case, when the pressures inside the first balloon and the second balloon become equal, the first balloon, which has a lower modulus of elasticity, expands first, and then, the second balloon expands. As a result, it is possible to expand the first balloon first and then the second balloon with a simple structure.

In the above-described aspect, the medical device may further include a temporary fixing part that releasably fixes the first balloon to the outer surface of the insertion part, the fluid may be supplied to or discharged from either the first balloon or the second balloon through the fluid supply path, and the fixed state achieved by the temporary fixing part may be released by a pressing force exerted in the longitudinal-axis direction by the second balloon.

With this structure, the fixed state achieved by the temporary fixing part is maintained until the pressing force exerted in the longitudinal-axis direction by the second balloon exceeds a predetermined value. Hence, the first balloon is expanded radially outward at its position without moving in the longitudinal-axis direction relative to the insertion part, and the pressure in the second balloon also increases.

Then, at the point when the pressing force exerted in the longitudinal-axis direction by the second balloon exceeds the predetermined value, the fixing achieved by the temporary fixing part is released, allowing the first balloon to move in the direction parallel to the longitudinal axis of the insertion part. As a result, the second balloon is expanded in the longitudinal-axis direction. As a result, it is possible to expand the first balloon first and then the second balloon with a simple structure.

REFERENCE SIGNS LIST 1 medical device (overtube)
2 insertion part
3 first balloon
4 second balloon
5 fluid supply path
8 center hole
9 outer tube (tubular part)
10 inner tube (tubular part)
14 connecting flow path
12 tube
18 temporary fixing part
X large intestine (body cavity)

The invention claimed is:
1. A medical device comprising:
an insertion part having a longitudinal axis;
a first balloon and a second balloon attached to the insertion part; and
a fluid supply path through which a fluid is supplied to or discharged from the first balloon and the second balloon, wherein
the first balloon is configured to expand and contract by the fluid in a direction intersecting the longitudinal axis and the first balloon is configured to be movable in the longitudinal-axis direction relative to the insertion part, the second balloon is configured to expand and contract by the fluid in the longitudinal-axis direction and the second balloon is disposed distally relative to the first balloon in the longitudinal-axis direction, a first end of the second balloon is fixed to a distal end of the insertion part, and a second end of the second balloon is fixed to the first balloon, and the fluid supply path comprises a connecting flow path communicating between a first inner space of the first balloon and a second inner space of the second balloon.

2. The medical device according to claim 1, wherein a first outside diameter of the first balloon when expanded is greater than a second outside diameter of the second balloon when expanded.

3. The medical device according to claim 1, wherein the first balloon comprises a ring shape having a center hole, and the insertion part is inserted through the center hole so as to be movable relative thereto in the longitudinal-axis direction.

4. The medical device according to claim 1, wherein the fluid supply path comprises a tube through which the fluid is supplied to or discharged from the first balloon, and the flow resistance of the fluid through the tube is smaller than the flow resistance of the fluid through the connecting flow path.

5. The medical device according to claim 4, wherein the tube enters the second inner space of the second balloon from the inside of the insertion part via a fixing position at which the second balloon is fixed to the insertion part and is connected to the first balloon via the second inner space of the second balloon.

6. The medical device according to claim 5, wherein the tube has a spiral shape around the longitudinal axis.

7. The medical device according to claim 6, wherein the inner space of the second balloon comprises a tubular shape by concentrically disposing two tubular parts having different outside diameters, and the tube is attached to a radially outer surface of the tubular part located on a radially inner side.

8. The medical device according to claim 1, wherein the second balloon is formed of a second material having a higher modulus of elasticity than a first material of the first balloon.

9. The medical device according to claim 1, further comprising a temporary fixing part configured to releasably fix the first balloon to an outer surface of the insertion part, wherein a fixed state achieved by the temporary fixing part is released by a pressing force exerted in the longitudinal-axis direction by the second balloon.

10. The medical device according to claim 1, wherein the second balloon is configured to be expanded after the first balloon is expanded by supplying the fluid through the fluid supply path.

11. The medical device according to claim 10, wherein the second balloon is configured to be contracted after the first balloon is contracted by discharging the fluid through the fluid supply path.

12. The medical device according to claim 1, wherein the insertion part is an overtube having an inner conduit for insertion of an endoscope.

13. A medical device comprising:

an insertion part having a longitudinal axis;

a first balloon configured to expand and contract in a direction intersecting the longitudinal axis;

a second balloon having a first end fixed to the insertion part and a second end fixed to the first balloon and the second balloon is configured expand and contract in a longitudinal-axis direction; and a fluid supply path through which a fluid is supplied to or discharged from the first balloon and the second balloon;

wherein the second balloon is disposed distally relative to the first balloon in the longitudinal-axis direction.

14. The medical device according to claim 13, wherein the second balloon is configured to be expanded after the first balloon is expanded by supplying the fluid through the fluid supply path.

15. The medical device according to claim 13, wherein the first balloon is supported so as to be movable in the longitudinal-axis direction relative to the insertion part, and the first end of the second balloon is fixed to the distal end of the insertion part, and the second end of the second balloon is fixed to the first balloon.

16. The medical device according to claim 14, wherein the second balloon is configured to be contracted after the first balloon is contracted by discharging the fluid through the fluid supply path.

17. The medical device according to claim 13, wherein the fluid supply path comprises a connecting flow path communicating between a first inner space of the first balloon and a second inner space of the second balloon.

18. The medical device according to claim 17, wherein the fluid supply path comprises a tube through which the fluid is supplied to or discharged from the first balloon, and the flow resistance of the fluid through the tube is smaller than the flow resistance of the fluid through the connecting flow path.

19. The medical device according to claim 17, wherein the fluid supply path comprises a tube through which the fluid is supplied to or discharged from the first balloon, and the fluid supply path enters the second inner space of the second balloon from the inside of the insertion part via a fixing position at which the second balloon is fixed to the insertion part and is connected to the first balloon via the second inner space of the second balloon.

20. The medical device according to claim 13, wherein the insertion part is an overtube having an inner conduit for insertion of an endoscope.

* * * * *